(12) United States Patent  (10) Patent No.: US 9,193,903 B2
Hayashi et al.  (45) Date of Patent: Nov. 24, 2015

(54) SOLID SCINTILLATOR, RADIATION DETECTOR, AND RADIATION EXAMINATION DEVICE

(71) Applicants: Kabushiki Kaisha Toshiba, Tokyo (JP); Toshiba Materials Co., Ltd., Yokohama-Shi (JP)

(72) Inventors: Makoto Hayashi, Yokohama (JP); Yukihiro Fukuta, Yokohama (JP); Takao Sawa, Yokohama (JP)

(73) Assignees: Kabushiki Kaisha Toshiba, Minato-Ku (JP); Toshiba Materials Co., Ltd., Yokohama-Shi (JP)

( * ) Notice: Subject to any disclaimer, the term of this patent is extended or adjusted under 35 U.S.C. 154(b) by 0 days.

(21) Appl. No.: 14/476,856

(22) Filed: Sep. 4, 2014

(65) Prior Publication Data

US 2015/0021485 A1 Jan. 22, 2015

Related U.S. Application Data

(63) Continuation of application No. PCT/JP2013/001735, filed on Mar. 14, 2013.

(30) Foreign Application Priority Data

Mar. 15, 2012 (JP) ................................ 2012-059477

(51) Int. Cl.
*G01T 1/10* (2006.01)
*C09K 11/77* (2006.01)
*A61B 6/03* (2006.01)
(Continued)

(52) U.S. Cl.
CPC .............. *C09K 11/7774* (2013.01); *A61B 6/03* (2013.01); *C01G 15/00* (2013.01); *G01N 23/046* (2013.01); *G01T 1/2023* (2013.01); *G21K 4/00* (2013.01); *A61B 6/4208* (2013.01); (Continued)

(58) Field of Classification Search
CPC ........................................................ G21K 4/00
USPC ...................................................... 250/361 R
See application file for complete search history.

(56) References Cited

U.S. PATENT DOCUMENTS 4,525,628 A 6/1985 DiBianca et al.
7,094,362 B2 8/2006 Setlur et al.
(Continued)

FOREIGN PATENT DOCUMENTS

CN 1922286 A 2/2007
CN 1927996 A 3/2007
(Continued)

OTHER PUBLICATIONS

International Search Report and Written Opinion (Application No. PCT/JP2013/001735) dated May 7, 2013.
(Continued)

*Primary Examiner* — Kiho Kim
(74) *Attorney, Agent, or Firm* — Burr & Brown, PLLC (57) ABSTRACT

A solid scintillator in an embodiment includes a polycrystal body of an oxide having a garnet structure. In the solid scintillator, a linear transmittance at a wavelength of 680 nm is 10% or more. The oxide constituting the solid scintillator has a composition represented by, for Example, General formula: $(Gd_{1-\alpha-\beta-\gamma}Tb_\alpha Lu_\beta Ce_\gamma)_3(Al_{1-x}Ga_x)_a O_b$, wherein $0<\alpha \leq 0.55$, $0<\beta \leq 0.55$, $0.0001 \leq \gamma \leq 0.1$, $\alpha+\beta+\gamma<1$, $0<x<1$, $4.8 \leq a \leq 5.2$, $11.6 \leq b \leq 12.4$.

14 Claims, 2 Drawing Sheets

(51) Int. Cl.

| | |
|---|---|
| *G21K 4/00* | (2006.01) |
| *G01N 23/04* | (2006.01) |
| *C01G 15/00* | (2006.01) |
| *G01T 1/202* | (2006.01) |
| *A61B 6/00* | (2006.01) |

(52) U.S. Cl.
CPC ...... *C01P 2006/90* (2013.01); *G01N 2223/419* (2013.01); *G21K 2004/06* (2013.01)

(56) References Cited

U.S. PATENT DOCUMENTS

| | | |
|---|---|---|
| 2003/0075706 A1 | 4/2003 | Shiang et al. |
| 2003/0127630 A1 | 7/2003 | Vartuli et al. |
| 2004/0084655 A1 | 5/2004 | Vartuli et al. |
| 2005/0082495 A1* | 4/2005 | Nakano et al. ............. 250/484.4 |
| 2008/0023650 A1* | 1/2008 | Isoda et al. ................ 250/484.4 |
| 2010/0187423 A1 | 7/2010 | Nakamura et al. |
| 2011/0024684 A1 | 2/2011 | Fukuta et al. |
| 2011/0260377 A1* | 10/2011 | Jiang ............................ 264/621 |
| 2012/0145962 A1 | 6/2012 | Fukuta et al. |

FOREIGN PATENT DOCUMENTS

| | | |
|---|---|---|
| EP | 2395065 A1 * | 12/2011 |
| EP | 2474590 A2 * | 7/2012 |
| JP | 58-204088 A1 | 11/1983 |
| JP | 59-27283 A1 | 2/1984 |
| JP | 59-045022 A1 | 3/1984 |
| JP | 2005-120251 A1 | 5/2005 |
| JP | 2005-126718 A1 | 5/2005 |
| JP | 2011-153200 A1 | 8/2011 |
| JP | 2012-072331 A1 | 4/2012 |
| WO | 2008/093869 A1 | 8/2008 |
| WO | 2009/113379 A1 | 9/2009 |

OTHER PUBLICATIONS

Li, Hui-li, et al., "Fabrication of Transparent Ce:LuAg Ceramics by a Solid-State Reaction Method." Journal of Inorganic Materials; vol. 21, No. 5, Sep. 2006 (6 pages).

Kamada, Kei, et al., "Composition Engineering in Cerium-Doped $(Lu, Gd)_3(Ga, Al)_5O_{12}$ Single-Crystal Scintillators." Crystal Growth & Design, vol. 11, Nov. 2011, p. 4484-4490 (7 pages).

Chinese Office Action (Application No. 201380014162.4) mailed Apr. 21, 2015 (with English Translation).

* cited by examiner

SOLID SCINTILLATOR, RADIATION DETECTOR, AND RADIATION EXAMINATION DEVICE

CROSS-REFERENCE TO RELATED APPLICATIONS

This application is a continuation of prior International Application No. PCT/JP2013/001735 filed on Mar. 14, 2013, which is based upon and claims the benefit of priority from Japanese Patent Application No. 2012-059477 filed on Mar. 15, 2012; the entire contents of all of which are incorporated herein by reference.

FIELD

Embodiments described herein relate generally to a solid scintillator, a radiation detector, and a radiation examination device.

BACKGROUND

In the fields of medical diagnosis and industrial nondestructive inspection, an X-ray examination device such as an X-ray computed tomographic photographing device (X-ray CT device) is used. The X-ray CT device has a structure in which an X-ray tube (X-ray source) to emit fan beam X-rays in a fan shape and an X-ray detector having many X-ray detecting elements arranged in parallel are arranged opposite each other with a tomographic surface of a specimen as a center. In the X-ray CT device, the fan beam X-rays are emitted from the X-ray tube to the X-ray detector, and, for Example, an angle is changed by one degree at a time with respect to the tomographic surface every time the emission is performed, and thereby collection of X-ray absorption data is performed. The X-ray absorption data are analyzed in a computer to calculate an X-ray absorptance at each position of the tomographic surface, and thereby an image according to the X-ray absorptances is constituted.

In the X-ray detector of the X-ray CT device, a solid scintillator to emit visible light by stimulation with X-rays is used. The solid scintillator is a single crystal scintillator or a polycrystalline ceramic scintillator. The development of an X-ray detector combined with such a solid scintillator and a photodiode is promoted. By using the X-ray detector using the solid scintillator, it is easy to increase the number of channels by downsizing the detecting element, and therefore high resolution of the X-ray CT device can be achieved.

As the solid scintillator to be used for the X-ray detector, there are known single crystal bodies such as cadmium tungstate ($CdWO_4$), sodium iodide (NaI), and cesium iodide (CsI), and polycrystalline ceramics such as europium-activated barium fluoride chloride (BaFCl:Eu), terbium-activated lanthanum oxybromide (LaOBr:Tb), thallium-activated cesium iodide (CsI:Tl), calcium tungstate ($CaWO_4$), cadmium tungstate ($CdWO_4$), europium-activated gadolinium oxide ($Gd_2O_3$:Eu), and praseodymium-activated gadolinium oxysulfide ($Gd_2O_2S$:Pr).

Rare earth oxysulfide ceramics such as $(Gd_{1-x}Rr_x)_2O_2S$ ($0.0001 \leq x \leq 0.01$) and $(Gd_{1-x-y}Pr_xCe_y)_2O_2S$ ($0.0001 \leq x \leq 0.01$, $0 \leq y \leq 0.005$) have properties of a large X-ray absorption coefficient and a short afterglow time of light emission. Apart from this, rare earth oxide ceramics having a garnet structure are also known as a solid scintillator. The rare earth oxide ceramics having a garnet structure have a property of excellent light output. However, in the X-ray CT device, an exposure dose of a subject is desirably further decreased. Therefore, the solid scintillator is required to achieve higher sensitivity and to decrease an afterglow time in order to shorten a scanning time.

On the other hand, in the security fields of a baggage inspection device and the like at an airport as antiterrorism measures attracting attention recently, a solid scintillator made of a single crystal body of cadmium tungstate is frequently used. The single crystal body of cadmium tungstate is inferior in properties to rare earth oxysulfide ceramics and rare earth oxide ceramics having a garnet structure, but is superior in cost to them because it is low in cost. However, the single crystal body of cadmium tungstate has a risk of worsening the environment because cadmium is a noxious substance. With regard to the rare earth oxide ceramics having a garnet structure, improvement in light output is achieved by improvement of an oxide composition or the like, but further improvement in properties is required.

DETAILED DESCRIPTION

According to one embodiment, there is provided a solid scintillator including a polycrystal body of an oxide having a garnet structure. In the solid scintillator of the embodiment, a linear transmittance at a wavelength of 680 nm is 10% or more.

Hereinafter, there will be explained a solid scintillator, a radiation detector, and a radiation examination device in an embodiment with reference to the drawings. The solid scintillator includes a polycrystal body of an oxide having a garnet structure (to be described as a garnet-type oxide, hereinafter). The solid scintillator in the embodiment is characterized in that a linear transmittance at a wavelength of 680 nm is 10% or more. The linear transmittance at a wavelength of 680 nm is preferably 20% or more.

The garnet-type oxide has a stoichiometric composition approximated by $R_3A_5O_{12}$. R is a rare earth element, A is at least one element selected from Al and Ga, and O is oxygen. Even if a garnet phase has a composition somewhat deviating from the stoichiometric composition, properties as a solid scintillator material can be obtained. Therefore, the solid scintillator in the embodiment only needs to include a polycrystal body of an oxide having a composition represented by $R_3A_aO_b$, (where a is a number (atomic ratio) satisfying $4.8 \leq a \leq 5.2$ and b is a number (atomic ratio) satisfying $11.6 \leq b \leq 12.4$). When the total atomic weight a of Al and Ga deviates from the range of 4.8 to 5.2 or when atomic weight b of oxygen deviates from the range of 11.6 to 12.4 with the atomic weight of the rare earth element R set to 3, heterophases such as a perovskite phase precipitate easily. The polycrystal body of the garnet-type oxide has a state where many oxide crystal grains aggregate to be integrated. The polycrystal body of the garnet-type oxide is desirably a sintered compact.

The solid scintillator in the embodiment has a linear transmittance of 10% or more when its linear transmittance is measured with light having a wavelength of 680 nm. The linear transmittance indicates a ratio of light transmitted vertically from the rear surface of a sample (straight advancing light) to light vertically entered the sample through the front surface (incident light). The linear transmittance is measured by using a sample having a thickness of 1 mm and having its front and rear surfaces polished to have surface roughness Ra of 1 μm or less. When the intensity of the incident light emitted to the front surface of the sample is set to $I_0$ and the intensity of the light transmitted vertically from the rear surface of the sample (straight advancing light) is set to I, a linear transmittance T is obtained from "$T=I/I_0 \times 100(\%)$." When the light having a wavelength of 680 nm is emitted to the polycrystal body of the garnet-type oxide, the polycrystal body of the garnet-type oxide does not emit light or emits just a little light. Thus, the light having a wavelength of 680 nm is effective for measuring the transmittance of the solid scintillator made of the polycrystal body of the garnet-type oxide.

Such a polycrystal body of the garnet-type oxide having a linear transmittance of 10% or more at a wavelength of 680 nm makes it possible to improve properties such as light output and sensitivity of the solid scintillator. That is, a radiation detector includes a photoelectric conversion element disposed on the rear of a solid scintillator array as will be described later. The linear transmittance at a wavelength of 680 nm of the solid scintillator is high, which means that the ratio at which emitted light of the solid scintillator excited by X-rays reaches the photoelectric conversion element as the straight advancing light increases. Thus, it becomes possible to improve light output, sensitivity, and the like of the solid scintillator array. The linear transmittance at a wavelength of 680 nm of the solid scintillator is more preferably 20% or more.

When light transmits through the polycrystal body, the light is reflected by bubbles, hetero-phases, crystal grain boundaries, and the like to be scattered. The linear transmittance being high means that the reflection of light caused by bubbles, hetero-phases, crystal grain boundaries, and the like is decreased to increase the ratio of the straight advancing light. That is, by decreasing the bubbles, hetero-phases, crystal grain boundaries, and the like existing in the polycrystal body of the garnet-type oxide, the linear transmittance at a wavelength of 680 nm can be made 10% or more, and further 20% or more. As a forming method of the polycrystal body, as will be described later, a hot pressing method, a HIP method (a hot isostatic pressing method), a vacuum sintering method, and the like can be cited. In the hot pressing method, graphite and the like are used, and in the HIP method, metal is used, so that in a sintering process, oxygen is extracted from crystals and oxygen deficiency is caused. In the vacuum sintering method, sintering is performed in a vacuum atmosphere, so that oxygen is similarly extracted during the sintering and oxygen deficiency is caused.

In spite of having the stoichiometric composition at the stage of the solid scintillator material (phosphor powder), oxygen deficiency is caused in the forming process of the polycrystal body (the sintering process). For the increase in the linear transmittance at a wavelength of 680 nm, it is effective to heat treat the polycrystal body of the garnet-type oxide in an oxygen-containing atmosphere as will be described later in detail. The polycrystal body (sintered compact) is heat treated in an oxygen-containing atmosphere, and thereby effects such as a decrease in hetero-phases, uniformity in crystal grain boundaries, removal of strain, and further improvement of oxygen deficiency can be obtained. These all contribute to suppression of the light scattering. Further, the light scattering caused by bubbles is decreased by increasing the density of the polycrystal body (sintered compact). Thereby, it becomes possible to increase the linear transmittance at a wavelength of 680 nm of the solid scintillator.

The polycrystal body of the garnet-type oxide constituting the solid scintillator in the embodiment preferably has a composition represented by Formula (1) below.

$$(Gd_{1-\alpha-\beta-\gamma}Tb_\alpha Lu_\beta Ce_\gamma)_3(Al_{1-x}Ga_x)_a O_b \qquad \text{General formula}$$

(in the formula, α, β, and γ are numbers (atomic ratios) satisfying $0<\alpha \leq 0.55$, $0<\beta \leq 0.55$, $0.0001 \leq \gamma \leq 0.1$, and $\alpha+\beta+\gamma<1$, x is a number (atomic ratio) satisfying $0<x<1$, a is a number (atomic ratio) satisfying $4.8 \leq a \leq 5.2$, and b is a number (atomic ratio) satisfying $11.6 \leq b \leq 12.4$).

In Formula (1), the rare earth element R is gadolinium (Gd), terbium (Tb), lutetium (Lu), and cerium (Ce). The garnet-type oxide as the material constituting the solid scintillator (solid scintillator material) may also contain rare earth elements other than these in the range of 50 mass ppm or less. Gd, Tb, and Lu are elements occupying eight-coordination sites. An electron beam irradiation surface of an X-ray tube target is made of tungsten and tungsten alloy (Re—W alloy or the like) in most cases. The X-ray tube has a mechanism to generate X-rays when an electron beam is applied to the electron beam irradiation surface made of tungsten and tungsten alloy.

Gd is preferable as a constituent element of the solid scintillator material because of having the highest absorption coefficient of X-rays to be generated from tungsten. Therefore, the amount of Gd with respect to the total amount of the rare earth elements R in Formula (1) (the total amount of Gd, Tb, Lu, and Ce) is set to an amount greater than zero ($0<1-\alpha-\beta-\gamma$ (or $\alpha+\beta+\gamma<1$)). Further, in order to stably obtain the garnet structure and to improve an amount of X-rays absorbed by the solid scintillator, the amount of Gd with respect to the total amount of the rare earth elements R is preferably 10 atomic % or more ($0.1 \leq 1-\alpha-\beta-\gamma$ (or $\alpha+\beta+\gamma \leq 0.9$)), and further is more preferably 20 atomic % or more ($0.2 \leq 1-\alpha-\beta-\gamma$ (or $\alpha+\beta+\gamma \leq 0.8$)).

Tb forms a basic structure of the garnet-type oxide together with Gd, and further is an element contributing also to light emission. The amount of Tb (α) with respect to the total amount of the rare earth elements R is set to be in the range of greater than zero to 55 atomic % or less ($0<\alpha \leq 0.55$). In this case, an afterglow property of the solid scintillator material improves. When the amount of Tb (α) exceeds 55 atomic %, the effect more than it cannot be obtained, and further the ratio of the component of the other rare earth elements is decreased, and thereby the properties deteriorate. The amount of Tb (α) with respect to the total amount of the rare earth elements R is, for improving a light emission property and an afterglow property, preferably in the range of not less than 10 atomic % nor more than 50 atomic % ($0.1 \leq \alpha \leq 0.5$), and is more preferably in the range of not less than 20 atomic % nor more than 30 atomic % ($0.2 \leq \alpha \leq 0.3$).

Lu is an element to suppress precipitation of hetero-phases in the garnet-type oxide. As the hetero-phase in the garnet-type oxide, a perovskite phase (R(Al, Ga)$O_3$ phase) and a monoclinic phase ($R_4$(Al, Ga)$_2O_9$ phase) are shown as an Example. As a concrete Example of the perovskite phase, $GdAlO_3$ is cited. As a concrete Example of the monoclinic phase, a $Gd_4Al_2O_9$ phase is cited. Particularly, the perovskite phase easily precipitates in the garnet-type oxide as a hetero-phase. When the precipitation amount of the perovskite phase increases, the light scattering is caused easily, resulting in that the properties of the solid scintillator material made of the garnet-type oxide deteriorate.

By using Lu as one of the rare earth elements R constituting the garnet-type oxide, the precipitation of the hetero-phases typified by the perovskite phase is suppressed. Thus, the properties such as light emission intensity of the solid scintillator material can be improved. The amount of Lu ($\beta$) with respect to the total amount of the rare earth elements R is set to be in the range of greater than zero to 55 atomic % or less ($0<\beta\leq0.55$). When the amount of Lu ($\beta$) is within the above-described range, the properties such as light emission intensity of the solid scintillator material improve. When the amount of Lu ($\beta$) exceeds 55 atomic %, the effect more than it cannot be obtained, and further the ratio of the component of the other rare earth elements is decreased, and thereby the properties deteriorate.

In order to obtain the effect of suppressing the precipitation of hetero-phases in the garnet-type oxide with good repeatability, the amount of Lu ($\beta$) with respect to the total amount of the rare earth elements R is preferably set to 1 atomic % or more. In order to secure the amounts of Gd and the like, the amount of Lu ($\beta$) is preferably set to 50 atomic % or less. As above, the amount of Lu ($\beta$) with respect to the total amount of the rare earth elements R is preferably in the range of not less than 1 atomic % nor more than 50 atomic % ($0.01\leq\beta\leq0.5$), and further is more preferably in the range of not less than 20 atomic % nor more than 50 atomic % ($0.2\leq\beta\leq0.5$).

Ce is an element to make the garnet-type oxide emit light. Even if the amount of Ce ($\gamma$) with respect to the total amount of the rare earth elements R is less than 0.01 atomic % and exceeds 10 atomic %, the light emission of the solid scintillator material made of the garnet-type oxide becomes weak. Therefore, the amount of Ce ($\gamma$) with respect to the total amount of the rare earth elements R is set to be in the range of not less than 0.01 atomic % nor more than 10 atomic % ($0.0001\leq\gamma\leq0.1$). The amount of Ce ($\gamma$) is more preferably in the range of not less than 0.1 atomic % nor more than 1 atomic % ($0.001\leq\gamma\leq0.01$).

Aluminum (Al) and gallium (Ga) are essential elements constituting the garnet structure. Al and Ga each are a single element to form the garnet structure. However, when Al alone is contained, an impurity (for Example, Ba) is taken in easily. On the other hand, when Ga alone is contained, there is a risk of weakening the light emission and increasing the cost. Therefore, the garnet-type oxide constituting the solid scintillator in the embodiment contains both Al and Ga. Thus, the amount of Ga (x) with respect to the total amount of Al and Ga in Formula (1) is set to be in the range of greater than zero to less than 100 atomic % ($0<x<1$).

Further, in order to achieve a decreasing effect of the content of impurities and an improving effect of the light emission property, the amount of Ga (x) with respect to the total amount of Al and Ga is preferably in the range of not less than 1 atomic % nor more than 80 atomic % ($0.01\leq x\leq0.8$). When the amount of Ga (x) is less than 1 atomic %, there is a risk that the decreasing effect of the content of impurities cannot be obtained sufficiently. On the other hand, when the amount of Ga (x) exceeds 80 atomic %, the light emission property is likely to deteriorate and the manufacturing cost is likely to increase. The amount of Gd (x) is more preferably in the range of not less than 10 atomic % nor more than 60 atomic % ($0.1\leq x\leq0.6$).

In composition-analyzing the garnet-type oxide, a quantitative analysis of Gd, Tb, Lu, Ce, Al, and Ga is set to be performed by alkali fusion-ICP emission spectrometry. A quantitative analysis of oxygen is set to be performed by an inert gas fusion-infrared absorption method.

In the garnet-type oxide constituting the solid scintillator, the garnet structure originally has a stoichiometric composition approximated by $R_3A_5O_{12}$ (R: rare earth element, A: Al, Ga). However, even if the garnet phase has a composition somewhat deviating from the stoichiometric composition, the properties as the solid scintillator material can be obtained. When the composition of the garnet structure is represented by $R_3A_aO_b$ with the total atomic weight of the rare earth elements R set to 3, total atomic weight a of Al and Ga is set to be in the range of $4.8\leq a\leq5.2$. When the total atomic weight a of Al and Ga deviates from the above-described range, hetero-phases such as a perovskite phase precipitate easily. The total atomic weight a of Al and Ga is preferably in the range of $4.9\leq a\leq5.1$.

When the total atomic weight of the rare earth elements R is set to 3, the atomic weight b of oxygen is set to be in the range of $11.6\leq b\leq12.4$. When the atomic weight b of oxygen deviates from the above-described range, hetero-phases such as a perovskite phase precipitate easily. The atomic weight b of oxygen is preferably in the range of $11.8\leq b\leq12.2$. Incidentally, the total atomic weight of the rare earth elements R($=3$) is set to the total atomic weight of Gd, Tb, Lu, and Ce. Even if other rare earth elements are contained, they do not have to be counted as the atomic weight of the rare earth element R because their contents are small to be 50 mass ppm or less.

Further, in the garnet-type oxide constituting the solid scintillator, the content of barium (Ba) as an impurity is preferably 400 mass ppm or less (including zero). The content of fluorine (F) as an impurity is preferably 300 mass ppm or less (including zero). If the content of Ba exceeds 400 mass ppm or the content of F exceeds 300 mass ppm, the transparency of the solid scintillator decreases and variations in light emission occur easily.

Ba easily reacts with Al, and there is a risk that Ba reacts with Al to form hetero-phases before the garnet phase is formed. Therefore, the content of Ba is preferably set to 400 mass ppm or less, and further is more preferably set to 200 mass ppm or less. However, Ba easily produces a liquid phase as BaF, thereby having an effect of activating formation reaction of the garnet phase. The garnet-type oxide may also contain Ba in the range of 10 to 400 mass ppm, and further in the range of 10 to 200 mass ppm. The content of F is preferably zero (a detection limit or less). The content of Ba is set to be quantified by alkali fusion-ICP emission spectrometry, and the content of F is set to be quantified by thermal hydrolysis separation-ion chromatography.

In manufacturing the garnet-type oxide (solid scintillator material), a flux such as barium fluoride ($BaF_2$) or aluminum fluoride ($AlF_3$) is preferably used as an reaction accelerator. Particularly, $BaF_2$ is effective for the manufacture of the garnet-type oxide. However, in the garnet-type oxide using Al only, Ba and F are easily taken into grains in the process of grain growth. Further, Ba and F easily react with Al to generate $BaAlO_x$ compound, (where x is mainly 3), or the like as a hetero-phase easily. With respect to such a point, Al and Ga are both used for the garnet-type oxide constituting the solid scintillator, thereby making it possible to prevent Ba and F from being taken into the garnet-type oxide more than necessary.

As described above, the garnet-type oxide constituting the solid scintillator preferably has a small precipitation amount of hetero-phases of a perovskite phase, and the like. Concretely, when an X-ray diffraction analysis of the solid scintillator is performed, a ratio ($I_P/I_G$) of a maximum peak intensity $I_P$ of the perovskite phase to a maximum peak intensity $I_G$ of the garnet phase is preferably 0.01 or less (including zero). If the ratio $I_P/I_G$ exceeds 0.01, the ratio of the hetero-phase increases, so that the light scattering is caused and the properties as the scintillator easily deteriorate. The ratio $I_P/I_G$ of the solid scintillator is more preferably zero (a detection limit or less). The X-ray diffraction analysis of the solid scintillator (or solid scintillator material) is set to be performed by using Cu as a target with a voltage of 40 kV, a current value of 40 mA, and a scan speed of 1.0°/min. The hetero-phases are preferably decreased at the stage of the solid scintillator material.

The ratio ($I_P/I_G$) of the maximum peak intensity (height) $I_P$ of the perovskite phase to the maximum peak intensity (height) $I_G$ of the garnet phase is 0.01 or less (including zero) in the X-ray diffraction analysis, which means that the perovskite phase being a hetero-phase is very small. When each maximum peak intensity of all the hetero-phases (a monoclinic phase, and the like) other than the perovskite phase is also compared with that of the garnet phase similarly, the intensity ratio is preferably 0.01 or less, and further is more preferably zero (a detection limit or less). That is, no hetero-phases preferably exist. The garnet-type oxide in which no hetero-phases exist or few hetero-phases exist makes it possible to improve the light emission intensity (light output) and the transparency of the solid scintillator.

Further, when the solid scintillator is excited by X-rays, the maximum light emission peak preferably exists in the range of 530 to 560 nm. The maximum light emission peak is based on a sharp light emission spectrum of Tb, and it is found that Tb contributes to light emission. Using both the sharp light emission spectrum of Tb and broad light emission spectrum of Ce makes it possible to provide a solid scintillator having high light output and having a short afterglow (a short decay time of afterglow). The existence of the maximum light emission peak in the above-described range indicates that the garnet-type oxide has few hetero-phases and has a stable crystal structure. Additionally, when the solid scintillator made of the garnet-type oxide is used to constitute a radiation detector, matching with a photodiode being a photoelectric conversion element improves, and sensitivity of the detector can be increased.

The polycrystal body constituting the solid scintillator preferably has an average crystal grain diameter in the range of 2 to 50 µm. The average crystal grain diameter of the polycrystal body is less than 2 µm, which means that a large number of crystal grains having a small crystal grain diameter exist. Therefore, the ratio of crystal grain boundaries increases and the light transmittance decreases easily. In order to increase the light transmittance of the solid scintillator, the average crystal grain diameter of the polycrystal body is preferably large. When the average crystal grain diameter is too large, the strength of the polycrystal body decreases, so that the average crystal grain diameter of the polycrystal body is preferably 50 µm or less. The average crystal grain diameter of the polycrystal body is more preferably in the range of 5 to 20 µm.

The average crystal grain diameter of the polycrystal body is measured by a line intercept method by using a SEM photograph (secondary electron image) at a magnification of 2000 times or more as a magnified photograph with a unit area of 200 µm×200 µm. That is, on the magnified photograph, a 200 µm straight line (having a line width of 0.5 mm or less) is drawn, and the number of grains existing on the straight line is counted. The average of crystal grain diameters is obtained from "Expression: 200 µm/the number of grains existing on the 200 µm straight line." An average value of the resultant obtained by performing this work three times is set to the "average crystal grain diameter." However, when it is difficult to determine grain boundaries, the average of crystal grain diameters may also be obtained by "Expression: 50 µm/the number of grains existing on a 50 µm straight line" with four magnified photographs with a "unit area of 50 µm×50 µm"× four photographs set as one unit area. This work may also be performed three times (the unit area of 50 µm×50 µm×12 photographs in total) to obtain the "average crystal grain diameter."

The relative density of the polycrystal body is preferably 99.5% or more, and is more preferably not less than 99.9% nor more than 100%. The relative density is obtained by "Expression: (an actual measured value/a theoretical value)× 100 (%)" with an actual measured value obtained by the Archimedes method and a theoretical value obtained from a lattice constant.

Further, of the solid scintillator, a diffuse transmittance of light having a wavelength of 680 nm is preferably 50% or more. The solid scintillator in the embodiment does not emit light at a wavelength of 680 nm, so that the wavelength is effective for measuring the diffuse transmittance. The diffuse transmittance is 50% or more, which means that the transparency is high. Further, by controlling the average crystal grain diameter and the relative density, the diffuse transmittance can be made 60% or more. This is because pores that decrease the diffuse transmittance almost disappear. Additionally, regarding the above-described garnet-type oxide, the polycrystal body can be obtained without using a sintering aid such as a silicon oxide, so that the crystal grain boundary is unlikely to cause the decrease in the diffuse transmittance. Incidentally, for the measurement of the diffuse transmittance, a solid scintillator having a thickness of 1 mm and having its front and rear surfaces polished to have the surface roughness Ra of 1 µm or less is used.

When the solid scintillator is excited by X-rays, the decay time until the afterglow becomes 5% is preferably 5 ms or shorter. In the garnet-type oxide constituting the solid scintillator in the embodiment, Tb and Ce are both used, thereby making it possible to provide a solid scintillator having large light output and having a short afterglow time. The decay time of afterglow indicates a time until the light output becomes 5% of the maximum value after completion of the excitation by X-rays when the maximum value of the light output is set to 100%. The decay time of afterglow is set to 5 ms or shorter, 4 ms or shorter, and further 2 ms or shorter, and thereby the radiation examination device can be switched on•off for a short time. Thus, it becomes possible to increase a scanning speed of the radiation examination device to make measurement efficient.

The shape of the solid scintillator is not limited in particular. As a typical shape of the solid scintillator, a rectangular parallelepiped having a height of not less than 0.5 mm nor more than 5 mm, a width of not less than 0.5 mm nor more than 5 mm, and a length of not less than 10 mm nor more than 40 mm can be cited. Also in a solid scintillator having such a rectangular parallelepiped shape, the above-described excellent properties such as the linear transmittance and the short afterglow can be obtained.

Next, there will be explained a method of manufacturing the solid scintillator material (phosphor powder) and the solid scintillator using it. The method of manufacturing the solid scintillator material and the solid scintillator is not limited in particular. As a method of efficiently manufacturing the solid scintillator material and the solid scintillator, the following method can be cited.

First, a gadolinium oxide ($Gd_2O_3$) powder, a terbium oxide ($Tb_4O_7$) powder, a lutetium oxide ($Lu_2O_3$) powder, a cerium oxide ($CeO_2$) powder, an aluminum oxide ($Al_2O_3$) powder, and a gallium oxide ($Ga_2O_3$) powder to be raw materials are mixed so as to have a target composition to prepare a raw material mixture. As the raw material powder, an oxide powder of each element is preferably used in order to efficiently obtain the garnet-type oxide.

Next, as a reaction accelerator, a flux such as barium fluoride ($BaF_2$) is mixed with the raw material mixture. The flux is preferably barium fluoride. The barium fluoride makes it easy to obtain a garnet-type oxide with few hetero-phases. Further, the barium fluoride is also effective for densification. The raw material mixture mixed with the flux may also be granulated. The additive amount of the flux is preferably set to be in the range of 2 to 6 parts by mass with respect to the raw material mixture set to 100 parts by mass. When the additive amount of the flux is less than 2 parts by mass, a reaction acceleration effect cannot be obtained sufficiently. When it exceeds 6 parts by mass, the flux is increased too much and hetero-phases are formed easily.

Burning after mixing the raw material mixture with the reaction accelerator is preferably performed at a temperature in the range of 1200 to 1800° C. When the burning temperature is lower than 1200° C., there is a risk that the reaction becomes insufficient. When the burning temperature exceeds 1800° C., the temperature is too high and thus the barium fluoride is vaporized easily, and thereby hetero-phases are formed easily. A burning atmosphere is preferably set to an inert atmosphere of an Ar gas or the like. Under certain circumstances, the burning may also be performed in a vacuum ($10^{-2}$ Pa or less) or in a reducing atmosphere. A burning time is preferably set to be in the range of 1 to 8 hours.

The raw material mixture is burned to then become an oxide powder having a garnet structure. However, the reaction accelerator remains in large amounts in the garnet-type oxide powder obtained after the burning. When the barium fluoride is used as the reaction accelerator, for Example, Ba and F in large amounts remain in the garnet-type oxide powder obtained after the burning. Therefore, the oxide powder obtained after the burning is preferably washed to wash the remaining reaction accelerator away. In order to efficiently perform the washing, it is also effective to crush and sieve the oxide powder obtained after the burning to bring its average grain diameter in the range of 0.5 to 20 μm.

The washing process is preferably performed by combining washing with a pure water (water from which impurities are removed with an ion exchange resin) and acid washing. A dilute hydrochloric acid is preferably used for the acid washing. The oxide powder obtained after the burning is washed with a dilute hydrochloric acid to then be washed with a pure water. This work is repeated several times, thereby making it possible to remove the remaining flux component. The washing with pure water is preferably performed until the pH of the pure water after the washing becomes 6 or more.

When, for Example, the barium fluoride is used as the reaction accelerator, the elements to remain are Ba and F. At this time, the oxide powder obtained after the burning is put into a washing vessel in a ratio of 5 to 30 vol % to the volume capacity of the washing vessel, and a dilute hydrochloric acid or pure water is added to perform the washing. After stirring for a certain period of time, the dilute hydrochloric acid or pure water is discarded. This work is repeated several times. F reacts with water easily to thus be removed relatively easily, resulting in that F becomes 300 mass ppm or less easily. When the washing process is performed five or more times, the amount of F can be decreased to zero (a detection limit or less). On the other hand, Ba is an element to be taken in by Al easily, so that a number of times of washing are needed for decreasing the amount of Ba to zero (a detection limit or less). Further, for decreasing the amount of Ba to less than 10 mass ppm, it is necessary to remove Ba that has been taken in once. On this occasion, small pores or defects occur to cause a decrease in the transparency. Therefore, the number of times of washing is preferably set to 5 to 10. Further, the content of Ba in the solid scintillator material is preferably set to 10 mass ppm or more also in view of suppressing the occurrence of pores or defects in the washing process.

The garnet-type oxide powder obtained after the washing is dried, thereby making it possible to obtain the solid scintillator material (phosphor powder). The average grain diameter of the garnet-type oxide powder is preferably in the range of 0.5 to 20 μm. Such a solid scintillator material is formed and sintered to manufacture the solid scintillator. As a sintering method, a hot pressing method, an HIP method, a vacuum sintering method, and the like can be cited. A sintering temperature is preferably 1400 to 1700° C., and a sintering time is preferably 1 to 10 hours. A pressure to be applied is preferably 20 MPa or more. A sintering atmosphere is preferably an inert atmosphere of an Ar gas or the like, or a vacuum atmosphere ($10^{-2}$ Pa or less). A sintered compact obtained in the sintering process becomes a polycrystal body. The forming process is preferably performed by die pressing, rubber pressing, or CIP (cold isostatic pressing).

When the garnet-type oxide powder is sintered, a sintering aid is not preferably used. When a sintering aid of $SiO_2$ or the like is used, a sintering property improves, but the sintering aid remains at grain boundaries to cause a decrease in the transparency of the sintered compact. Further, the existence of the sintering aid leads to the decrease in the linear transmittance. Therefore, the sintering aid is not preferably used. The above-described solid scintillator material is excellent in sintering property, so that a densified solid scintillator (solid scintillator having a relative density of 99.5% or more) can be obtained without using the sintering aid. Further, the garnet-type oxide powder having an average grain diameter in the range of 0.5 to 20 μm is used, thereby making it easy to obtain a sintered compact (polycrystal body) having an average crystal grain diameter in the range of 2 to 50 μm.

The sintered compact can be used as it is as a solid scintillator depending on the size of the obtained sintered compact (polycrystal body). When the size of the sintered compact is large, the sintered compact is cut into a required size to be used as a solid scintillator. In other words, it is also possible that a plate-shaped sintered compact having a large size is manufactured and then a solid scintillator is cut out therefrom to be manufactured. The cutting-out process is performed by using a multi-wire saw or the like. The front surface of the sintered compact may also be polished according to need. The sintered compact is preferably heat treated in an oxygen-containing atmosphere after the sintering process and after the cutting-out process for the purpose of strain removal, uniformity in crystal grain diameter, decrease in oxygen deficiency, and the like. The heat treatment is preferably performed under the condition of 1000 to 1400° C.×2 to 6 hours. As the oxygen-containing atmosphere at the heat treatment, an air atmosphere and a gas atmosphere containing oxygen in the range of 5 to 100 vol % (with its balance of an inert gas such as nitrogen) can be cited. Between both of them, the air is preferable because its cost is low.

The heat treatment is performed on the sintered compact in the oxygen-containing atmosphere as described above, thereby making it possible to achieve the strain removal, uniformity in crystal grain diameter, decrease in oxygen deficiency, uniformity in crystal and crystal grain boundary, and the like. These make it possible to improve the linear transmittance of the solid scintillator. As described above, the sintering process is performed under a pressurized environment or under a vacuum environment. At this time, oxygen is extracted from the front surface of the sintered compact (solid scintillator), and partial oxygen deficiency is caused easily. When the partial oxygen deficiency is caused, variations in composition of each garnet-type oxide crystal occur. These variations cause the decrease in the linear transmittance. The sintered compact is heat treated in the oxygen-containing atmosphere, thereby making it possible to decrease the oxygen deficiency and further making it possible to achieve the uniformity in crystal composition and crystal grain boundary. Thus, the linear transmittance of the solid scintillator improves.

Figure 1:
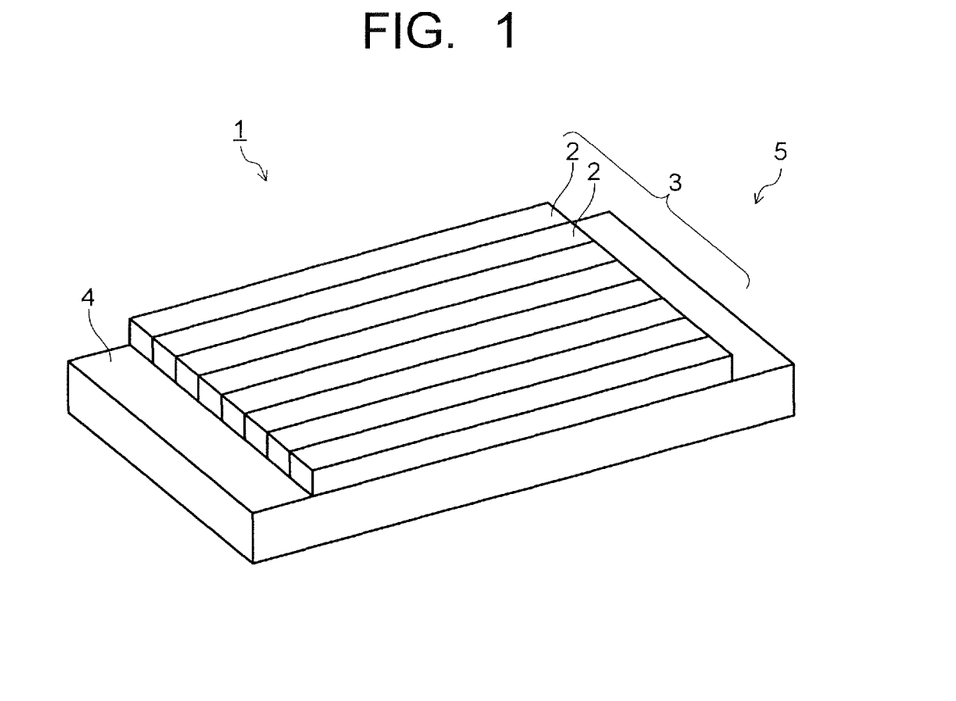
FIG. 1 is a perspective view showing a radiation detector in a first embodiment.

Next, there will be explained the radiation detector and the radiation examination device in the embodiment. FIG. 1 shows a radiation detector 1 according to a first embodiment. The radiation detector 1 includes a plurality of solid scintillators 2, 2, . . . . The solid scintillator 2 is made of the polycrystal body of the garnet-type oxide in the embodiment. The plural solid scintillators 2 are two-dimensionally arranged via a reflection layer (not shown) to form a solid scintillator block 3 integrated in its length direction. A photoelectric conversion element 4 is integrally disposed under the solid scintillator block 3, and by these, a solid scintillator array 5 is constituted.

Figure 2:
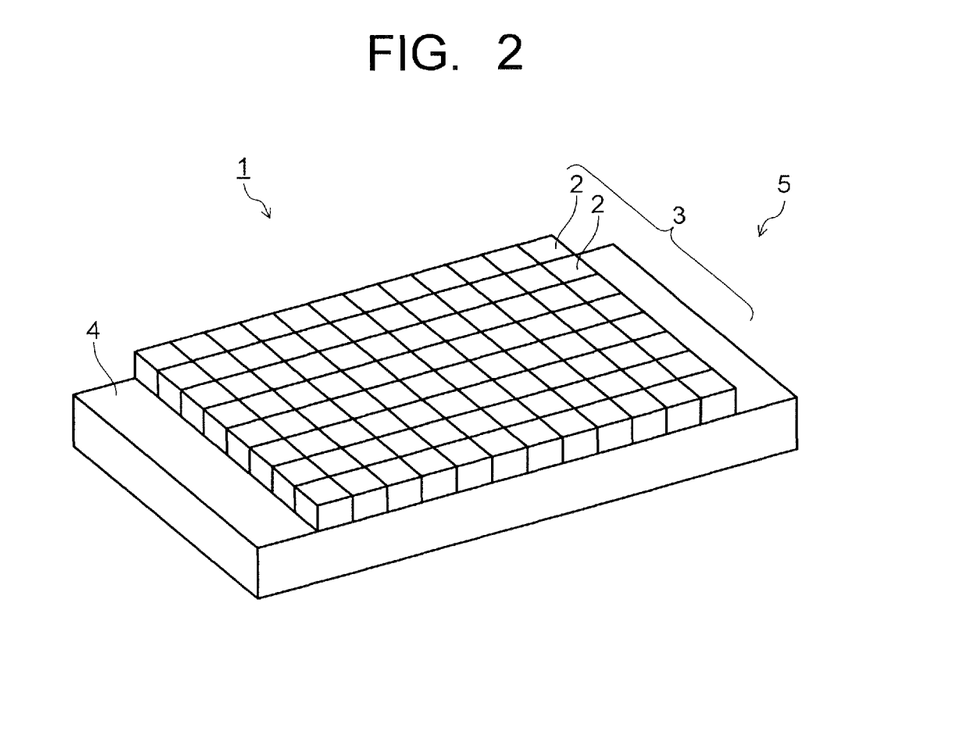
FIG. 2 is a perspective view showing a radiation detector in a second embodiment

The shape of the solid scintillator 2 is not limited to a rectangular parallelepiped shape shown in FIG. 1. The solid scintillator 2 may also have a dice shape shown in FIG. 2. In a radiation detector 1 shown in FIG. 2, dice-shaped solid scintillators 2 are arranged in a grid pattern via a reflection layer (not shown) to form a solid scintillator block 3 integrated in its length direction and its width direction. As the photoelectric conversion element 4, for Example, a photodiode is used. An electrical signal wiring (not shown) and a collimator (not shown) from the photoelectric conversion element 4 are attached to the solid scintillator array 5, and thereby the radiation detector 1 in the embodiment is constituted.

Figure 3:
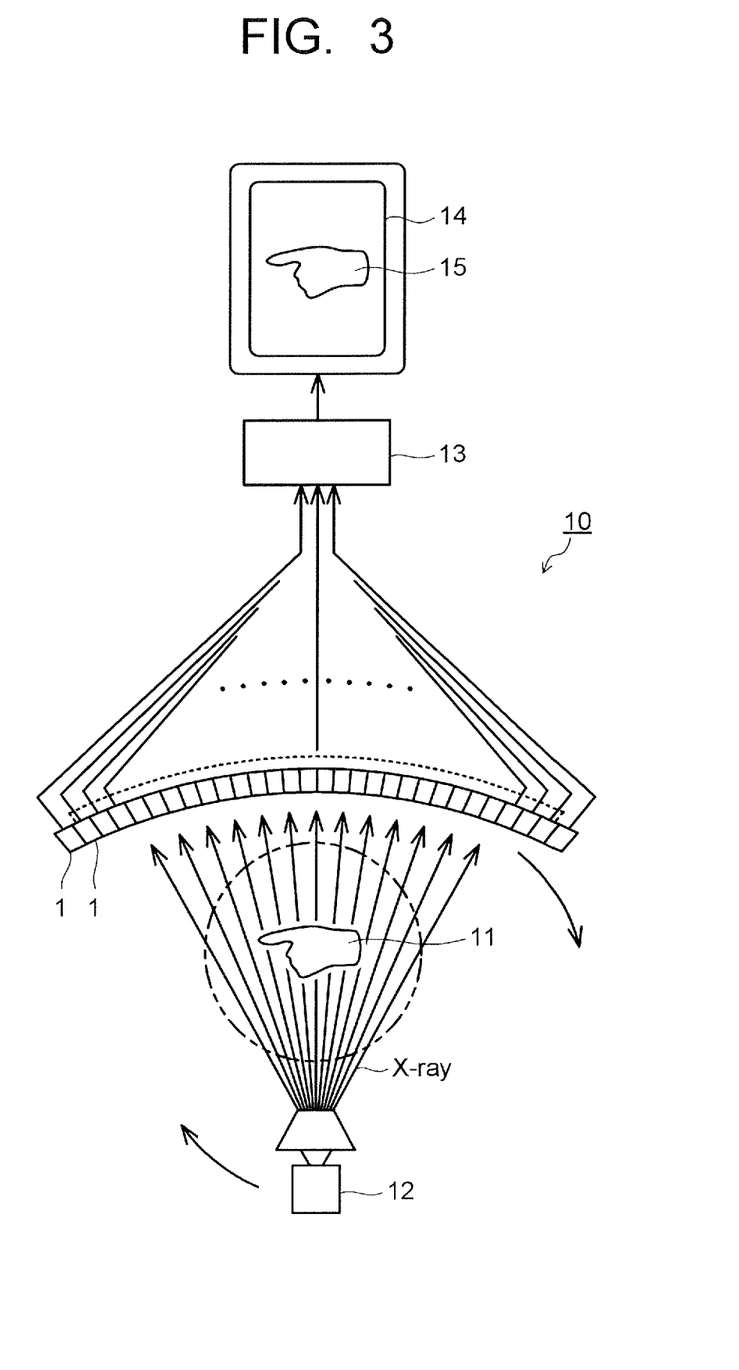
FIG. 3 is a conceptual view showing a radiation examination device in an embodiment.

FIG. 3 shows an X-ray CT device 10 being one Example of the radiation examination device in the embodiment. The X-ray CT device 10 is provided with the plural radiation detectors 1, 1, . . . . The radiation detectors 1 are disposed to face an X-ray tube 12 with a specimen 11 therebetween. X-rays emitted from the X-ray tube 12 transmit through the specimen 11 to reach the radiation detectors 1. In the radiation detector 1, the solid scintillator 2 emits light according to the X-rays transmitted through the specimen 11, and this emitted light is converted into an electrical signal in the photoelectric conversion element 4. The electrical signals are reconstituted in a computer 13, and thereby a specimen image 15 is shown on a monitor 14. The X-ray CT device 10 is constituted so that the specimen image 15 can be shown in three dimensions by measuring the specimen 11 in a manner to change an angle while moving the X-ray tube 12 along the specimen 11.

The radiation detector 1 in the embodiment is provided with the solid scintillators 2 each made of the polycrystal body of the garnet-type oxide excellent in light emission property, afterglow property, and the like. Further, the polycrystal body of the garnet-type oxide constituting the solid scintillator 2 has an excellent light transmittance, few heterophases, and controlled grain boundaries and pores. Thus, it is possible to provide the radiation detector 1 having high light output and having a short afterglow. The X-ray CT device 10 using the radiation detectors 1 as above makes it possible to perform photographing by high-speed scanning. Therefore, X-ray photographing with high sensitivity can be achieved while decreasing an X-ray exposure dose of a specimen. FIG. 3 shows the X-ray CT device, but the radiation examination device in the embodiment is not limited to this. The radiation examination device in the embodiment is effectively used also for an examination device of things other than human bodies such as a baggage inspection device.

Next, Examples and their evaluation results will be described.

EXAMPLES 1 TO 5, COMPARATIVE EXAMPLE 1

As raw material powders, a gadolinium oxide ($Gd_2O_3$) powder, a terbium oxide ($Tb_4O_7$) powder, a lutetium oxide ($Lu_2O_3$) powder, a cerium oxide ($CeO_2$) powder, an aluminum oxide ($Al_2O_3$) powder, and a gallium oxide ($Ga_2O_3$) powder were prepared. These raw material powders were mixed in predetermined ratios to be further mixed with a flux of $BaF_2$. The additive amount of the flux of $BaF_2$ was set to 4 to 5 parts by mass with respect to 100 parts by mass of the total amount of the raw material powders.

Next, the mixture of the raw material powders and the flux of $BaF_2$ was burned in an Ar atmosphere under the condition of 1400° C.×3 hours, and thereby a garnet-type oxide having a composition represented by $(Gd_{0.49}Tb_{0.2}Lu_{0.3}Ce_{0.01})_3(Al_{0.6}Ga_{0.4})_5O_{12}$ was obtained. This was crushed and sieved to make a powder having an average grain diameter of 5 to 15 μm. This powder was washed by alternately using a dilute hydrochloric acid and a pure water, and thereby a solid scintillator material (phosphor powder) was obtained. The washing process was performed in a manner that the powder was put into a washing vessel to be 20 vol % of the washing vessel and was stirred.

The one with the washing process performed one time was set to Example 1. The one with the washing process performed three times was set to Example 2. The one with the washing process performed five times was set to Example 3. The one with the washing process performed eight times was set to Example 4. The one with the washing process performed 10 times was set to Example 5. A drying process was performed after the washing process, and thereby solid scintillator materials (phosphor powders) of Examples were each obtained. In each Example, the pH of the washing water after the final pure water washing was 6 or more.

The average grain diameter, the content of Ba, and the content of F of the solid scintillator materials of Examples 1 to 5 were measured. X-ray diffraction of each of the solid scintillator materials was performed to obtain the maximum peak intensity $I_G$ of a garnet phase, the maximum peak intensity $I_P$ of a perovskite phase, and the ratio ($I_P/I_G$) of them. A wavelength of the maximum light emission peak when each of the solid scintillator materials was excited by X-rays was measured. These measurement results are shown in Table 1. As Comparative Example 1, a garnet-type oxide powder (solid scintillator material) having a composition represented by $(Gd_{0.5}Tb_{0.49}Ce_{0.01})_3Al_5O_{12}$ was prepared. The same measurement was also performed on this. Its results are also shown in Table 1.

TABLE 1

| | Solid Scintillator Material | | | | | |
|---|---|---|---|---|---|---|
| | Number of Times of Washing (Times) | Average Grain Diameter [μm] | Content of Ba [Mass ppm] | Content of F [Mass ppm] | Ratio $I_P/I_G$ | Maximum Light Emission Peak |
| Example 1 | 1 | 5 | 137 | 54 | 0 | 545 |
| Example 2 | 3 | 10 | 89 | 8 | 0 | 545 |

TABLE 1-continued

| | Solid Scintillator Material | | | | |
|---|---|---|---|---|---|
| | Number of Tunes of Washing (Times) | Average Grain Diameter [μm] | Content of Ba [Mass ppm] | Content of F [Mass ppm] | Ratio $I_P/I_G$ | Maximum Light Emission Peak |
| Example 3 | 5 | 15 | 24 | 0 | 0 | 545 |
| Example 4 | 8 | 10 | 15 | 0 | 0 | 545 |
| Example 5 | 10 | 10 | 12 | 0 | 0 | 545 |
| Comparative Example 1 | 5 | 10 | 450 | 126 | 0.03 | 545 |

As is clear from Table 1, the solid scintillator materials of Examples 1 to 5 each had the content of Ba in the range of 10 to 400 mass ppm and the content of F being 300 mass ppm or less (including zero). Lu was added, so that a perovskite phase being a hetero-phase was not detected. As a result of the X-ray diffraction, it was found that hetero-phases other than the perovskite phase are also not detected and the solid scintillator materials are each in a state having no hetero-phases. It was confirmed that as long as the number of times of washing is five or more times, the amount of F becomes zero (a detection limit or less). On the other hand, in Comparative Example 1, Lu and Ga were not used, so that a hetero-phase (perovskite phase) was detected. It was found that the content of Ba and the content of F are considerably large as compared to example in which the washing was performed the same number of times. This is conceivably because no Ga was used and thus Ba in large amounts was taken in by Al.

Next, sintered compacts (polycrystal bodies) were manufactured by using the above-described solid scintillator materials (phosphor powders). The sintering process was performed by a HIP treatment under the condition of 1600° C.×3 hours and the pressure of 50 MPa. The obtained sintered compacts were each cut into a size of 1.5 mm in height×1.5 mm in width×25 mm in length with a multi-wire saw. Thereafter, a heat treatment of 1200° C.×3 hours was performed in the air, and solid scintillators were obtained. A sintering aid was not used in the sintering process. The content of Ba, the content of F, and the ratio $I_P/I_G$ of each of the obtained solid scintillators and the wavelength of the maximum light emission peak when each of the solid scintillators was excited by X-rays were the same as the measurement values of each of the solid scintillator materials.

The relative density, the average crystal grain diameter of the polycrystal body, the linear transmittance at a wavelength of 680 nm, and the diffuse transmittance at a wavelength of 680 nm of each of the obtained solid scintillators were measured. The average crystal grain diameter of the polycrystal body was obtained by a line intercept method by using three magnified photographs with a unit area of 200 μm×200 μm. The linear transmittance and the diffuse transmittance were obtained by the intensity of light transmitted through the solid scintillator from its rear surface when light having a wavelength of 680 nm was emitted. The values of the linear transmittance before and after the heat treatment in the air were examined. These results are shown in Table 2.

Next, the above-described solid scintillators were used to manufacture radiation detectors. The 10 solid scintillators each having a size of 1.5 mm in height×1.0 mm in width×25 mm in length were arranged via a reflection layer to be integrated to then be disposed on a photodiode. An X-ray of 120 KVp was emitted to each of the radiation detectors as above and each light output was measured. The X-ray was emitted to the front surface of each of the scintillators through a 20-mm Al filter used for blocking soft X-rays, and the value of current flowing through the photodiode was obtained as the light output. Its results are shown in Table 2. The light output is expressed as a relative value (%) to light output of a single crystal scintillator of $CdWO_4$ set to 100.

TABLE 2

| | Solid Scintillator | | | | | |
|---|---|---|---|---|---|---|
| | Relative Density [%] | Average Crystal Grain Diameter [μm] | Linear Transmittance* | | Diffuse Transmittance [%]* | Light Output [%] |
| | | | Before Heat Treatment | After Heat Treatment | | |
| Example 1 | 99.9 | 8 | 11 | 16 | 58 | 150 |
| Example 2 | 99.9 | 15 | 20 | 31 | 62 | 154 |
| Example 3 | 99.9 | 27 | 24 | 37 | 68 | 158 |
| Example 4 | 99.9 | 16 | 25 | 39 | 68 | 160 |
| Example 5 | 99.9 | 16 | 27 | 41 | 68 | 165 |
| Comparative Example 1 | 98.5 | 20 | 3 | 4 | 47 | 142 |

*AT WAVELENGTH OF 680 nm

As shown in Table 2, in Examples, the solid scintillators each having a relative density of 99.5% or more were obtained without using a sintering aid. The solid scintillators in Examples were each high in linear transmittance and diffuse transmittance and were each excellent in light output. Further, it was also found that by the heat treatment in the oxygen-containing atmosphere, improvement in the linear transmittance is seen. On the other hand, the solid scintillator in Comparative Example had many hetero-phases to be inferior in the transmittance. Further, the light output was also inferior to that of Examples.

EXAMPLES 6 TO 12

A gadolinium oxide ($Gd_2O_3$) powder, a terbium oxide ($Tb_4O_7$) powder, a lutetium oxide ($Lu_2O_3$) powder, a cerium oxide ($CeO_2$) powder, an aluminum oxide ($Al_2O_3$) powder, and a gallium oxide ($Ga_2O_3$) powder were mixed in predetermined ratios to have each composition shown in Table 3 and were further mixed with a flux of $BaF_2$. The additive amount of the flux of $BaF_2$ was set to 2 to 6 parts by mass with respect to 100 parts by mass of the total amount of the raw material powders.

Next, each mixture of the raw material powders and the flux of $BaF_2$ was burned in an Ar atmosphere under the condition of 1400 to 1700° C.×2 to 5 hours, and thereby garnet-type oxide powders having the compositions shown in Table 3 were obtained. Next, the garnet-type oxide powders were each put into a washing vessel in the range of 5 to 30 vol % of the washing vessel to then be subjected to a washing process in which washing is performed by alternately using a dilute hydrochloric acid and a pure water three to five times repeatedly. The manufacturing conditions are shown in Table 4. The powders obtained after the washing process were each crushed and sieved to control the average grain diameter. The pH of the washing water after the final pure water washing was 6 or more. The properties of solid scintillator materials obtained in this manner were measured in the same manner as that in EXAMPLE 1. Their results are shown in Table 5.

TABLE 3

Scintillator Composition

| | |
|---|---|
| Example 6 | $(Gd_{0.199}Tb_{0.4}Lu_{0.4}Ce_{0.001})_3(Al_{0.8}Ga_{0.2})_{5.1}O_{11.9}$ |
| Example 7 | $(Gd_{0.37}Tb_{0.3}Lu_{0.3}Ce_{0.03})_3(Al_{0.6}Ga_{0.4})_{4.9}O_{12.1}$ |
| Example 8 | $(Gd_{0.49}Tb_{0.3}Lu_{0.2}Ce_{0.01})_3(Al_{0.4}Ga_{0.6})_5O_{12}$ |
| Example 9 | $(Gd_{0.48}Tb_{0.25}Lu_{0.25}Ce_{0.02})_3(Al_{0.5}Ga_{0.5})_5O_{12}$ |
| Example 10 | $(Gd_{0.39}Tb_{0.25}Lu_{0.35}Ce_{0.01})_3(Al_{0.9}Ga_{0.1})_5O_{12}$ |
| Example 11 | $(Gd_{0.135}Tb_{0.4}Lu_{0.45}Ce_{0.015})_3(Al_{0.3}Ga_{0.7})_5O_{12}$ |
| Example 12 | $(Gd_{0.28}Tb_{0.25}Lu_{0.45}Ce_{0.02})_3(Al_{0.6}Ga_{0.4})_5O_{12}$ |

TABLE 4

Manufacturing Conditions of Solid Scintillator Material

| | Additive Amount of $BaF_2$ [Mass %] | Burning Temperature/Time [° C./hr] | Number of Times of Washing [Times] |
|---|---|---|---|
| Example 6 | 5 | 1700/4 | 5 |
| Example 7 | 5 | 1400/5 | 5 |
| Example 8 | 3 | 1600/2 | 3 |
| Example 9 | 4 | 1700/4 | 4 |
| Example 10 | 5 | 1700/4 | 5 |
| Example 11 | 4 | 1600/3 | 4 |
| Example 12 | 5 | 1500/4 | 5 |

TABLE 5

Solid Scintillator Material

| | Average Grain Diameter [μm] | Content of Ba [Mass ppm] | Content of F [Mass ppm] | Ratio $I_P/I_G$ | Maximum Light Emission Peak [nm] |
|---|---|---|---|---|---|
| Example 6 | 14 | 320 | 182 | 0 | 545 |
| Example 7 | 11 | 53 | 3 | 0.01 | 545 |
| Example 8 | 8 | 36 | 0 | 0 | 546 |
| Example 9 | 8 | 27 | 0 | 0 | 546 |
| Example 10 | 13 | 79 | 0 | 0.01 | 545 |
| Example 11 | 8 | 20 | 0 | 0 | 545 |
| Example 12 | 9 | 45 | 0 | 0 | 545 |

As shown in Table 5, the solid scintillator materials in Examples 6 to 12 each had few hetero-phases (perovskite phases). In Comparative Example 1 described above, the amount of Lu was less than 0.01, so that many hetero-phases (perovskite phases) were detected. Thus, it is found that the amount of Lu is preferably 0.01 or more. In Examples 6 and 10 each having a relatively large amount of Al, Ba in relatively large amounts remained because of Ba being taken in easily. Thus, the amount of Al(1−x) with respect to the total amount of Al and Ga is desirably in the range of $0.3<1-x<0.9$.

Next, the above-described solid scintillator materials (phosphor powders) were used to manufacture sintered compacts (polycrystal bodies). The sintering process was performed by a HIP treatment under the condition of 1400 to 1700° C.×2 to 5 hours and the pressure of 30 to 60 MPa. The sintering conditions are shown in Table 6. A sintering aid was not used in the sintering process. The obtained sintered compacts were each cut into a size of 2 mm in height×2 mm in width×25 mm in length with a multi-wire saw. Next, a heat treatment in an oxygen-containing atmosphere was performed under the conditions shown in Table 6, and thereby intended solid scintillators were obtained. Further, as Reference Example 1, one obtained by replacing the heat treatment in the oxygen-containing atmosphere in Example 8 with a heat treatment in a nitrogen atmosphere was prepared.

TABLE 6

Sintering Conditions

| | Burning | | Heat Treatment Conditions | |
|---|---|---|---|---|
| | Temperature/Time [° C./hr] | Pressure [MPa] | Atmosphere [vol %] | Temperature/Time [° C./hr] |
| Example 6 | 1500/5 | 50 | Air | 1400/2 |
| Example 7 | 1400/5 | 60 | Air | 1100/5 |
| Example 8 | 1500/4 | 50 | Oxygen 10% + Nitrogen 90% | 1300/3 |
| Example 9 | 1700/2 | 30 | Oxygen 100% | 1200/5 |
| Example 10 | 1600/3 | 30 | Oxygen 50% + Nitrogen 50% | 1000/6 |
| Example 11 | 1500/5 | 50 | Oxygen 70% + Nitrogen 30% | 1300/4 |
| Example 12 | 1400/4 | 50 | Oxygen 5% + Nitrogen 95% | 1100/3 |
| Reference Example 1 | 1500/4 | 50 | Nitrogen 100% | 1300/3 |

The relative density, the average crystal grain diameter of the polycrystal body, the linear transmittance at a wavelength of 680 nm, and the diffuse transmittance at a wavelength of 680 nm of each of the obtained solid scintillators were measured in the same manner as that in Example 1. These results are shown in Table 7. Next, the solid scintillators were used to manufacture radiation detectors. The 15 solid scintillators each having a size of 2 mm in height×2 mm in width×25 mm in length were arranged via a reflection layer to be integrated to then be disposed on a photodiode. Each light output of the radiation detectors as above was measured in the same manner as that in Example 1. Its results are shown in Table 7.

TABLE 7

Solid Scintillator

| | Relative Density [%] | Average Crystal Grain Diameter [μm] | Linear Transmittance* Before Heat Treatment | Linear Transmittance* After Heat Treatment | Diffuse Transmittance [%]* | Light Output [%] |
|---|---|---|---|---|---|---|
| Example 6 | 99.9 | 35 | 13 | 21 | 53 | 152 |
| Example 7 | 99.9 | 18 | 9 | 14 | 51 | 146 |
| Example 8 | 100 | 14 | 24 | 38 | 67 | 158 |
| Example 9 | 100 | 22 | 25 | 41 | 69 | 162 |
| Example 10 | 99.9 | 21 | 8 | 12 | 47 | 140 |
| Example 11 | 100 | 17 | 26 | 39 | 68 | 159 |
| Example 12 | 99.9 | 20 | 16 | 24 | 60 | 154 |
| Reference Example 1 | 100 | 14 | 24 | 23 | 52 | 150 |

*AT WAVELENGTH OF 680 nm

As shown in Table 7, the solid scintillators of Examples 6 to 12 each exhibited excellent properties. The content of Ba, the content of F, and the ratio $I_P/I_G$ of each of the obtained solid scintillators and the intensity of the maximum light emission peak when each of the solid scintillators was excited by X-rays were the same as the measurement values of the solid scintillator materials. This is because sintering can be performed without using a sintering aid. Further, as is clear from Reference Example 1, in the case of the heat treatment in the atmosphere with 100% nitrogen, no improvement in the linear transmittance was confirmed.

EXAMPLES 1A to 12A, COMPARATIVE EXAMPLE 1A

The solid scintillators of Examples 1 to 12 and Comparative Example 1 were used to manufacture radiation detectors (Examples 1A to 12A and Comparative Example 1A), of which each decay time until an afterglow becomes 5% was examined. By using an X-ray tube (an electron beam irradiation surface made of Re—W alloy) to be an X-ray source of an X-ray CT device, X-rays were emitted to each of the radiation detectors of Examples 1 to 12A and Comparative Example 1A. The decay time until each light output becomes 5% of the maximum value after completion of the excitation by X-rays, where the maximum value of the light output was set to 100%, was measured. Its results are shown in Table 8.

TABLE 8

| | Solid Scintillator | Decay Time until Afterglow Becomes 5% [ms] |
|---|---|---|
| Example 1A | Example 1 | 1.7 |
| Example 2A | Example 2 | 0.8 |
| Example 3A | Example 3 | 0.8 |
| Example 4A | Example 4 | 0.7 |
| Example 5A | Example 5 | 0.7 |
| Example 6A | Example 6 | 2.8 |
| Example 7A | Example 7 | 3.5 |
| Example 8A | Example 8 | 0.8 |
| Example 9A | Example 9 | 0.9 |
| Example 10A | Example 10 | 4.4 |
| Example 11A | Example 11 | 0.9 |
| Example 12A | Example 12 | 2.3 |
| Comparative Example 1A | Comparative Example 1 | 8.0 |

As shown in Table 8, in each of the radiation detectors of Examples 1 to 12, the decay time of afterglow is 5 ms or shorter, which is extremely short. Radiation examination devices (X-ray CT devices) using the radiation detectors as above each can be switched on•off for a short time. Thus, high-speed scanning of the X-ray CT device is made possible, resulting in that it is possible to decrease an exposure dose of a subject during an examination.

While certain embodiments have been described, these embodiments have been presented by way of Example only, and are not intended to limit the scope of the inventions. Indeed, the novel embodiments described herein may be embodied in a variety of other forms; furthermore, various omissions, substitutions and changes in the form of the embodiments described herein may be made without departing from the spirit of the inventions. The accompanying claims and their equivalents are intended to cover such forms or modifications as would fall within the scope and spirit of the inventions.

What is claimed is:

1. A solid scintillator, comprising:
a polycrystal body of an oxide having a garnet structure, and a composition requested by a general formula:

$(Gd_{1-\alpha-\beta-\gamma}Tb_\alpha Lu_\beta Ce_\gamma)_3(Al_{1-x}GA_x)_a O_b$ where, $\alpha$, $\beta$, and $\gamma$ are numbers, which are atomic ratios, satisfying $0<\alpha<0.55$, $0<\beta\leq0.55$, $0.0001\leq\gamma\leq0.1$, and $\alpha+\beta+\gamma<1$, x is a number, which is an atomic ratio, satisfying $0<x<1$, a is a number, which is an atomic ratio, satisfying $4.8\leq a\leq5.2$, and b is a number, which is an atomic ratio, satisfying $11.6\leq b\leq12.4$, wherein a linear transmittance at a wavelength of 680 nm is 10% or more.

2. The solid scintillator according to claim 1, wherein the linear transmittance at the wavelength of 680 nm is 20% or more.

3. The solid scintillator according to claim 1, wherein $\alpha$ satisfies $0.1\leq\alpha\leq0.5$, $\beta$ satisfies $0.01\leq\beta\leq0.5$, and x satisfies $0.01<x\leq0.8$.

4. The solid scintillator according to claim 1, wherein the total amount of $\alpha$, $\beta$, and $\gamma$ satisfies $\alpha+\beta+\gamma\leq0.9$.

5. The solid scintillator according to claim 1, wherein a content of barium is 400 mass ppm or less, including zero.

6. The solid scintillator according to claim 1, wherein a content of fluorine is 300 mass ppm or less, including zero.

7. The solid scintillator according to claim 1, wherein a ratio ($I_P/I_G$) of a maximum peak intensity $I_P$ of a perovskite phase to a maximum peak intensity $I_G$ of a garnet phase by X-ray diffraction is 0.01 or less, including zero.

8. The solid scintillator according to claim 1, wherein a maximum light emission peak when the solid scintillator is excited by an X-ray exists in a range of from 530 to 560 nm.

9. The solid scintillator according to claim 1, wherein a decay time until an afterglow becomes 5% is 5 ms or less.

10. The solid scintillator according to claim 1, wherein an average crystal grain diameter of the polycrystal body is in a range of from 2 to 50 μm.

11. The solid scintillator according to claim 1, wherein a relative density of the polycrystal body is 99.5% or more.

12. The solid scintillator according to claim 1, wherein a diffuse transmittance at a wavelength of 680 nm is 50% or more.

13. A radiation detector comprising the solid scintillator according to claim 1.

14. A radiation examination device comprising the radiation detector according to claim 13.

* * * * *